US00PP18849P2

(12) United States Plant Patent
Truscott

(10) Patent No.: US PP18,849 P2
(45) Date of Patent: May 27, 2008

(54) CHERRY TREE 'KOOTENAY'

(50) Latin Name: *Prunus Avium L*
Varietal Denomination: Kootenay

(76) Inventor: William L. Truscott, 3102 Highway 3, Creston, British Columbia (CA), VOB 1G1

( * ) Notice: Subject to any disclaimer, the term of this patent is extended or adjusted under 35 U.S.C. 154(b) by 83 days.

(21) Appl. No.: 11/490,444

(22) Filed: Jul. 19, 2006

(51) Int. Cl.
*A01H 5/00* (2006.01)

(52) U.S. Cl. ..... Plt./181

(58) Field of Classification Search ..... Plt./181
See application file for complete search history.

*Primary Examiner*—Annette H Para
(74) *Attorney, Agent, or Firm*—Wells St. John P.S.

(57) ABSTRACT

A new and distinct variety of cherry tree denominated varietally as 'Kootenay' is described, and which is characterized as to novelty by a date of maturity for commercial harvesting and shipment which is approximately 9 to about 18 days later than the fruit produced by the "Lapins" cherry tree (unpatented) when grown under the ecological conditions prevailing near Creston, British Columbia, Canada.

2 Drawing Sheets

BACKGROUND OF THE NEW VARIETY

The present invention relates to a new, novel and distinct variety of cherry tree, "*Prunus Avium L*" and which has been denominated varietally as 'Kootenay'.

ORIGIN

The present variety of cherry tree was discovered as a whole tree mutation growing within the cultivated region of my orchard that was planted in 1992, and which is located near Creston, British Columbia, Canada. The whole tree mutation was discovered within a block of "Lapins" cherry trees (unpatented), and which were then growing on Mazzard rootstock (also unpatented). At the time of its discovery, which occurred on Aug. 4, 1996, the tree was noted as producing fruit which were mature for harvesting and shipment consistently later than the adjacent "Lapins" cherry trees then growing in the same block.

ASEXUAL REPRODUCTION

Asexual reproduction of this new and distinct variety of cherry tree was accomplished in the same orchard located near Creston, British Columbia by removing bud wood from the original whole tree mutation and thereafter budding it into test trees then growing on Mazzard rootstock (unpatented) that were then growing in the same orchard. This second generation asexual propagation took place during the 1997 growing season. Since that time, the inventor has continually observed these second generation asexually reproduced trees, and have observed and considered the characteristics of these trees, and the fruit produced thereby, and it would appear from his observations, that the characteristics of the originally discovered mutated tree, and its fruit, were established and appear to be transmitted through the succeeding asexual propagations.

SUMMARY OF THE VARIETY

'Kootenay' is a new and distinct variety of cherry tree which produces a sweet cherry which is somewhat similar in its characteristics to the fruit produced by the "Lapins" cherry tree (unpatented) both in terms of its wood, leaf bloom and other fruit morphology. However, 'Kootenay' is distinguishable from the "Lapins" cherry tree, and characterized principally as to novelty by producing fruit which has a date of maturity for harvesting and shipment between August 14$^{th}$ and August 20$^{th}$ under the ecological conditions prevailing near the orchard of origin. This date of harvesting is at least nine days later than the date of harvesting of the "Lapins" cherry tree at the same geographical location. In addition to the foregoing, the present variety is distinct therefrom by producing fruit which are much firmer than the fruit produced by the "Lapins" cherry tree when grown under the same ecological conditions prevailing near Creston, British Columbia.

BRIEF DESCRIPTION OF THE DRAWINGS

The accompanying drawings which are provided are color photographs of the present cherry tree variety.

Figure 1:
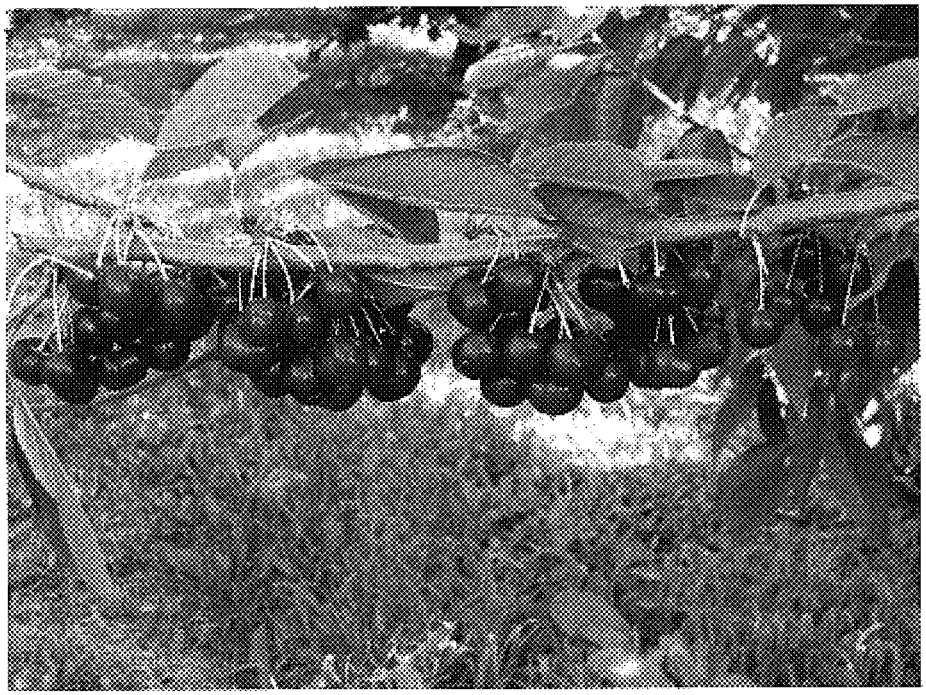
FIG. 1 depicts a fruiting branch of the 'Kootenay' cherry tree.
Figure 2:
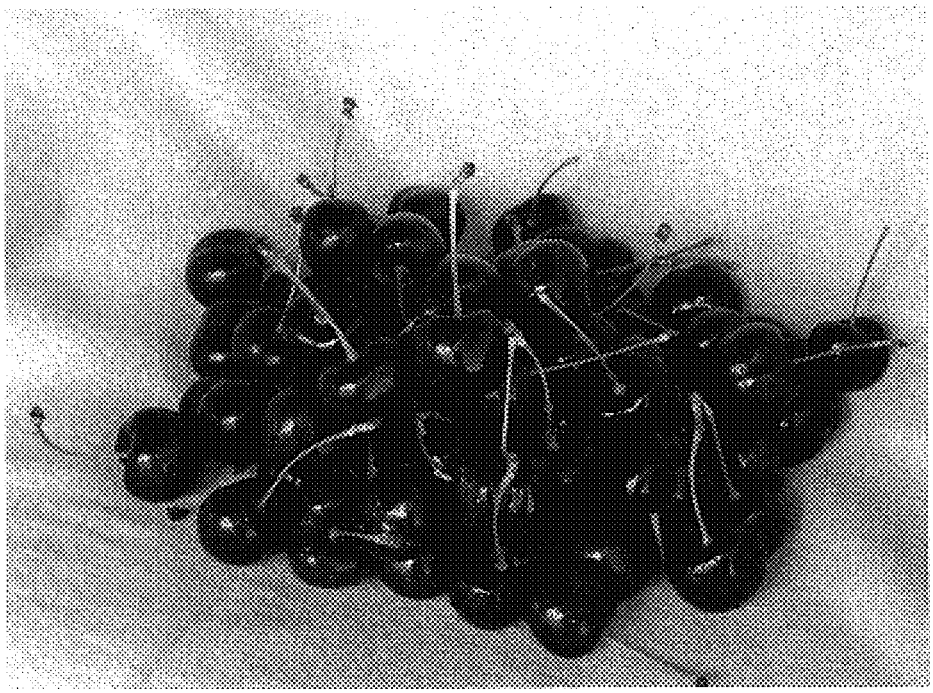
FIG. 2 is a second view of the fruit produced by the 'Kootenay' cherry tree following the harvesting of same.
Figure 3:
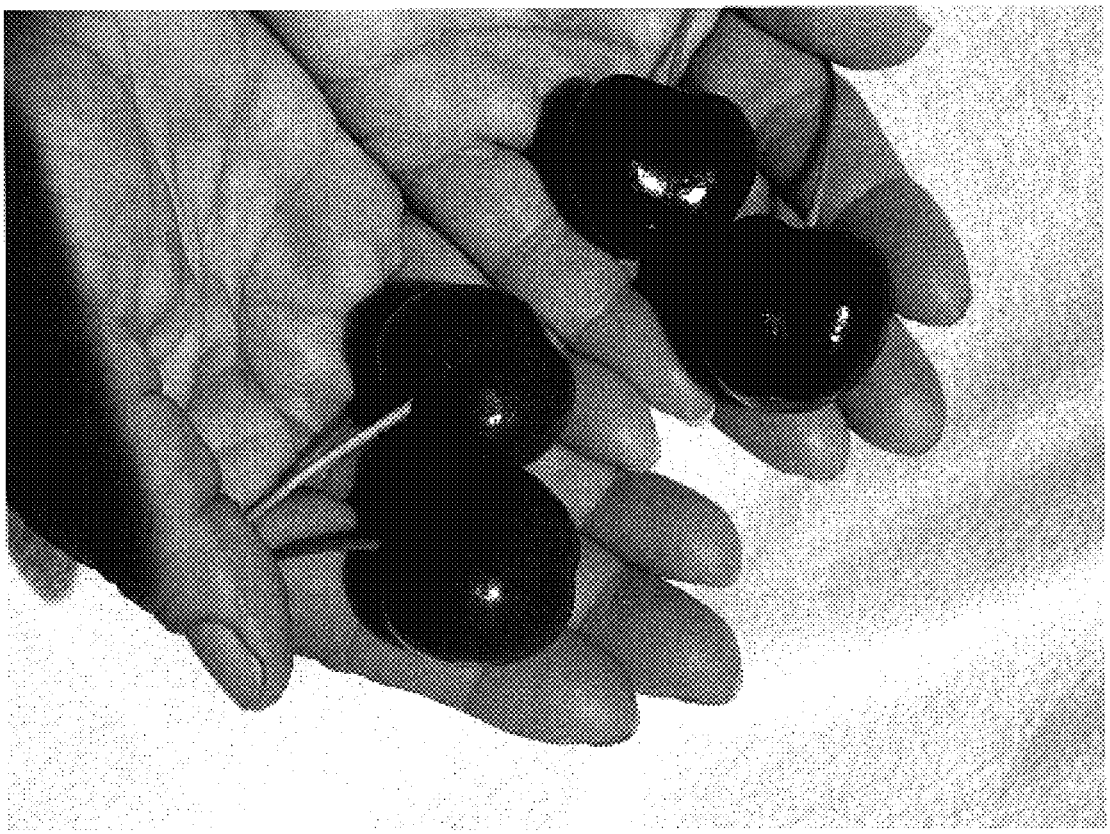
FIG. 3 shows a relative comparison of the fruit produced by the 'Kootenay' cherry tree (left) as compared to the fruit produced by the "Lapins" cherry tree (right).

The external coloration of the fruit as shown in these photographs is sufficiently matured for harvesting and shipment. The colors as seen in these photographs are as nearly true as is reasonably possible in a color representation of this type. Due to chemical development, processing and printing, the leaves and fruit depicted in these photographs may or may not be accurate when compared with the actual specimen. For this reason, future color references should be made to the referenced color plates (Royal Horticulture Society), and the descriptions provided for hereinafter.

DETAILED DESCRIPTION

Referring more specifically to the pomological details of this new and distinct variety of cherry tree, the following has been observed during the fourth fruiting season under the ecological conditions then prevailing at the orchard of the inventor which is located near the town of Creston, British Columbia, Canada. All major color code designations are made by reference to the R.H.S. Colour Chart, 4$^{th}$ Edition provided by The Royal Horticulture Society of Great Britain.

Tree:

*Size.*—Generally — Large. In this regard, the original mutated tree, which is now 13 years old, has a height of about 18 feet and further has a width, or crown spread of about 18 feet.

*Vigor.*—Considered vigorous. The average amount of growth on the original, chance mutated tree is about 83 cm per year.

*Branching habit.*—Considered upright and spreading.

*Density.*—Considered moderate for the species. As a general matter, the variety appears to form many spurs.

*Tree form.*—The original chance mutation has a rounded head.

*Hardiness.*—Considered hardy when grown under the ecological conditions prevailing in Creston, British Columbia, Canada.

*Productivity.*—Considered productive and similar to the "Lapins" cherry tree (unpatented).

*Regularity of bearing.*—Regular and consistent.

Trunk:

*Size.*—Considered stocky for the variety. Typically, the new variety has a diametral dimension of about 18 cm when measured at a distance of about 20 cm above the soil surface at commercial maturity.

*Bark surface texture.*—Normal for the species and typical for sweet cherries.

*Bark color.*—Brown, (N 200C).

Branches:

*Bark surface texture.*—Not distinctive and typical of sweet cherry trees, in general.

*Scaffold branches.*—Size — Considered stocky and having a diametral dimension of about 7 to about 9 cm.

*Crotch angle.*—Typically about 55 to about 75 degrees when measured from the horizontal plane. It should be understood, however, that this characteristic is not distinctive of the present variety.

*Bark color.*—First year wood — Green, (144A).

*Bark color.*—Second year wood — Gray-Brown, (N 199A).

*Bark color.*—Scaffold wood — Gray-Purple, (187A).

*Lenticels.*—First year wood — Considered numerous and mostly round, although some elongated lenticels may be found.

*Lenticels size.*—First year wood — About 1 to 2 mm long; and about 1 to about 2 mm wide.

*Lenticels color.*—First year wood — Gray-Orange, (165C).

*Lenticels.*—Second year wood — Considered numerous, elongated and positioned along the horizontal plane.

*Lenticels size.*—Second year wood — About 2.5 to 4 mm long; and about 1 to about 2 mm. wide.

*Lenticel color.*—Second year wood — Gray-Orange, (165A).

*Lenticels.*—Scaffold wood — Considered numerous, and oriented along the horizontal plane, and having a length dimension of about 6 to about 12 mm, and a width dimension of about 1 to about 3 mm.

Leaves:

*Size.*—Generally — Considered relatively large for the species. All leaf measurements are from vigorous, upright, current season growth which were taken at approximately mid-shoot.

*Leaf length.*—About 16.1 mm.

*Leaf width.*—About 8.1 cm.

*Leaf form.*—Generally speaking the leaf is lanceolate, and further having an acuminate tip.

*Leaf color.*—Dorsal surface — Yellow-green, (147A).

*Leaf color.*—Ventral surface — Yellow-green, (147B).

*Mid-vein.*—Size — Considered large for the species, about 2 to about 3 mm in diameter.

*Mid-vein.*—Underside color — Yellow-green, (145A).

*Leaf petiole.*—Length — Considered average for the species, and about 3.6 cm in length.

*Leaf petiole.*—Upper surface color — Grey-Purple, (187B).

*Leaf petiole.*—Lower surface color — Yellow-green, (146C).

*Leaf texture.*—Glabrous.

*Leaf marginal form.*—Doubly serrate.

*Leaf glands.*—Numbers — Variable in number, from about 2 to about 5.

*Leaf glands.*—Shape — Oval.

*Leaf glands.*—Width — About 2.5 mm.

*Leaf glands.*—Length — About 3 mm.

*Leaf glands.*—Position — Positioned in both the opposite and alternative positions on the rim of the petiolar groove and positioned about 5 to 10 mm from the leaf blade.

*Leaf stipules.*—Generally — Present, and having an average length of about 15 mm.

Flower:

*Flower buds.*—Hardiness — Generally speaking, the flower buds are hardy and similar to those produced by the "Lapins" cherry tree (unpatented).

*Flower buds.*—Length — About 8.12 mm.

*Flower buds.*—Width — About 5.03 mm.

*Flower buds.*—Form — Considered plump and conical.

*Date of first bloom.*—Over the last 5 years, the average date of first bloom has been about April 28$^{th}$ under the ecological conditions prevailing near Creston, British Columbia, Canada. This date of first bloom is some 3 to 5 days after the date of first bloom of the "Lapins" cherry trees growing under the same ecological conditions.

*Flowers.*—Size — Considered large for the species and having an average diameter of about 3.8 cm.

*Flowers.*—Color — White. This color is not distinctive of the present variety.

*Bloom count.*—Generally speaking, the present variety produces an average of 3 to 4 flowers per bud.

*Petals.*—Color — White. This color is not distinctive of the present variety.

*Petals.*—Width — About 13.4 mm.

*Petals.*—Length — About 15.9 mm.

*Floral nectaries.*—Color — Yellow-green, (144B).

*Anthers.*—Size — Considered small for the species, and oval in shape.

*Anthers.*—Length — About 1.0 mm.

*Anthers.*—Width — About 0.75 mm.

*Anthers.*—Color — Gray-orange, (N 167B).

*Pollen production.*—Present, and when mature, the pollen has a yellow-orange color (14B).
*Pedicel.*—Length — About 36.4 mm.
*Pedicel.*—Color — Yellow-green, (144D).
*Sepals.*—Form — Appearing in a fashion where they are curled backwards and lay flat against the pedicel.
*Sepals.*—Color — Yellow-green, (143D), and having moderate surface and tip highlights that appear reddish-purple (59B).

Fruit:
*Maturity when described.*—Ripe for harvesting and shipment about August 14$^{th}$-20$^{th}$ under the ecological conditions prevailing near the orchard of origin which is located near Creston, British Columbia, Canada. This date of harvesting is at least 9 to about 18 days later than the fruit produced on the "Lapins" cherry tree (unpatented) which is growing near the same geographical location, and under similar ecological conditions.
*Size.*—Generally — Considered large for the species.
*Average diameter which is transverse across the suture.*—About 2.7 cm.
*Average diameter in the apical plane.*—About 2.6 cm.
*Fruit form.*—Generally — Uniform and considered more reniform than round in shape.
*Fruit suture.*—Generally — Considered very shallow and not raised. The fruit suture has a color which is slightly darker than the adjacent skin.
*Fruit base.*—Considered rounded.
*Fruit apex.*—Having a rounded pistil point and being slightly indented.
*Fruit stem.*—Generally — Considered moderate in length for the species, and thin.
*Fruit stem.*—Length — About 4.3 cm.
*Fruit stem.*—Color — Green, (138C).
*Fruit skin.*—Thickness — Considered medium for the species.
*Fruit skin.*—Texture — Considered average.
*Fruit skin.*—Tenacity — Considered tenacious to flesh.
*Fruit skin.*—Tendency to crack — The present variety appears resistant to cracking similar to the "Lapins" cherry tree when grown under similar ecological conditions.
*Down.*—Generally — Wanting.
*Fruit skin color.*—Grey-purple, (187B).
*Fruit firmness.*—Generally — Firmness is rated on a scale of 1 to 10 with 10 being the firmest fruit. On average, the present variety 'Kootenay' produces fruit which consistently has a firmness of greater than 8. In contrast, the fruit produced by the "Lapins" cherry tree (unpatented), under the same ecological conditions, produces fruit having a firmness of less than about 7.2.
*Flesh color.*—Red-purple, (59B).
*Pit cavity color.*—Purple, (N 77A).
*Flesh texture.*—Considered firm and crisp.
*Flesh fibers.*—Numbers — Moderate.
*Ripening.*—Considered even.
*Flesh flavor.*—Sweet and having low acidity.
*Flesh aroma.*—Considered slight.
*Eating quality.*—Considered very good for the species.

Stone:
*Attachment.*—Considered semi-freestone.
*Size.*—Generally — Medium for the species.
*Average length.*—About 11.5 mm.
*Average width.*—About 10.9 mm.
*Stone form.*—Considered oval.
*Stone base.*—Shape — Rounded.
*Helium.*—Shape — Oblong.
*Stone apex.*—Shape — Rounded to round-conical in shape.
*Stone size.*—Surface area — Considered equal.
*Stone surface texture.*—Considered glabrous.
*Ventral edge.*—Form — A narrow suture about 1 mm wide extends along the ventral edge, and is subtended by two low ridges which converge basally and apically. These ridges are about 6 mm wide when measured at the mid-point.
*Dorsal edge.*—Form — Considered sharp and smooth and forming a slightly raised ridge which extends from the base to the apex.
*Stone.*—Color — Gray-orange, (164C).
*Tendency to split.*—Not observed.
*Fruit use.*—Considered a late season premium market cherry for local and long distance markets.
*Keeping quality.*—Considered excellent for the variety.
*Resistance to insects and diseases.*—The 'Kootenay' cherry tree shows no unusual susceptibilities or resistance to any disease and/or plant or fruit pests which normally infect sweet cherry trees.
*Shipping quality.*—Excellent.

Although the new variety of cherry tree possesses the described characteristics as a result of the growing conditions prevailing near the orchard of origin which is located in Creston, British Columbia, Canada, it is to be understood that variations in the usual magnitude, and characteristics incident to growing conditions, fertilization, pruning and pest control are to be expected.

NOT A COMMERCIAL WARRANTY

The foregoing detailed description has been prepared solely to comply with the provisions of 35 U.S.C. §112. It does not constitute a commercial warranty either expressed or implied that the present variety of cherry tree will in the future display all the botanical, pomological or other characteristics as set forth herein. Therefore this disclosure may not be relied upon to support any future legal claims including, but not limited to breach of warranty of merchantability, or fitness for any particular purpose which is directed in whole or in part to the present variety.

Having thus described and illustrated my new variety of cherry tree, what I claim is new, and desire to secure by Plant Letters Patent is:

1. A new and distinct variety of cherry tree substantially as illustrated and described, and which is denominated varietally as 'Kootenay' and which is further characterized principally as to novelty by producing fruit which are ripe for harvesting and shipment about August 14$^{th}$ to August 20$^{th}$ under the ecological conditions prevailing near Creston, British Columbia, Canada.

* * * * *